United States Patent [19]
Sablotsky et al.

[11] Patent Number: 4,814,168
[45] Date of Patent: Mar. 21, 1989

[54] TRANSDERMAL MULTIPOLYMER DRUG DELIVERY SYSTEM

[75] Inventors: Steven Sablotsky, Miami, Fla.; John M. Questel, Cuyahoga Falls; Dorothy J. Leeson, North Canton, both of Ohio

[73] Assignee: Noven Pharmaceuticals, Inc., Miami, Fla.

[21] Appl. No.: 164,482

[22] Filed: Mar. 4, 1988

[51] Int. Cl.$^4$ .............................. A61K 31/74
[52] U.S. Cl. ..................... 424/78; 424/449; 424/448; 424/485; 424/486; 424/484
[58] Field of Search ............ 424/484, 485, 486, 449, 424/78, 448

[56] References Cited

U.S. PATENT DOCUMENTS

| | | | |
|---|---|---|---|
| 4,144,317 | 3/1979 | Higuchi et al. | 424/432 |
| 4,421,737 | 12/1988 | Ito et al. | 424/448 |
| 4,668,232 | 5/1987 | Wolff et al. | 424/449 |
| 4,743,249 | 5/1988 | Loveland | 424/447 |

FOREIGN PATENT DOCUMENTS

| | | |
|---|---|---|
| 2095108 | 9/1982 | United Kingdom . |
| 2105990 | 4/1983 | United Kingdom . |
| 2161073 | 1/1986 | United Kingdom . |

OTHER PUBLICATIONS

Air Products and Chemicals, Inc., Technical Brochures for AIRFLEX® 400 TM (1979), p. 3.
U.S.I. Chemicals "Adhesives and Coating Manual" (unknown date).

Primary Examiner—Thurman K. Page
Assistant Examiner—L. R. Horne
Attorney, Agent, or Firm—Sybil Meloy

[57] ABSTRACT

A dermal compositon comprising a drug, a multipolymer of vinyl acetate, polyethylene and optionally one or more monomers, a natural or synthetic rubber and a tackifying agent. The ratio of the multipolymer to the rubber is, respectively, about 1:1 to about 10:1 and more preferably 1:1 to 5:1 and more preferably 3:1. The dermal composition can optionally contain a crosslinking agent, tackifiers, penetration enhancers and other ingredients known for use in adhesives for the transdermal delivery of drugs. The dermal compositions can be produced by a variety of methods known in the preparation of drug containing adhesive preparations including the homogenous mixing of the multi-polymer, drug and optional crosslinking agent and additional ingredients in aqueous solution followed by removal of excess water.

14 Claims, No Drawings

TRANSDERMAL MULTIPOLYMER DRUG DELIVERY SYSTEM

BACKGROUND OF THE INVENTION

The use of a pressure sensitive adhesive containing a medicament, i.e., a drug, a means of drug delivery through the skin at essentially a constant rate, is well known.

Known delivery systems involve incorporation of a medicament into the pressure sensitive adhesive formulation. The pressure sensitive adhesive must adhere effectively to the skin and then permit migration of the medicament from the pressure sensitive adhesive through the skin and into the blood stream of the patient.

Transdermal pressure sensitive adhesive formulations, such as nitrate vasodilators, may involve high concentrations (10 to 40% by weight) of the medicament in the adhesive. This type and high concentration of medicament markedly reduces the desirable adhesion properties of the adhesive, particularly when the drug serves as a plasticizer, namely a solvent, for the adhesive. The result is a marked reduction in the cohesive strength of the adhesive. Thus, peel adhesion, tack and shear resistance suffer undesirably due to the medicament addition. The incorporation of crosslinking agents for reactive functional groups of the polymer may, for example, enhance the formulation's shear resistance, but at the expense of tack and peel adhesion.

The use of presently marketed nitrate vasodilators in a pressure sensitive adhesive has been reported to frequently result in partial or total debonding, as early as during the first 24 hours of wearing by the patient. This debonding occurs as the patient perspires, exercises, or undertakes the normal physical activities expected in such a situation. The undesirable debonding results in a reduced rate of medication delivery and a total dosage reduction proportional to the area of the devce which is no longer in contact with the skin. A stronger adhesive, namely one having higher peel adhesion, shear resistance and tack, and in addition being perspiration resistant, would more effectively resist such undesirable debonding.

Previous adhesives have used as their starting polymer one that is inherently tacky. This invention starts with a non-tacky adhesive.

SUMMARY OF THE INVENTION

This invention is directed to a dermal composition suitable for use in the transdermal delivery of drugs, which composition permits a high loading of medicament into the formulation while maintaining acceptable shear, tack and peel adhesive properties.

The dermal composition of this invention comprises a drug, a multi-polymer comprising vinyl acetate and ethylene monomers; a rubber, and a tackifying agent. The multi-polymer and rubber are preferably in a ratio, respectively, from about 1:1 to about 10:1, more desirably about 1:1 to 5:1 and preferably about 3:1. The multi-polymer can be a copolymer, or terpolymer also including an acrylic and/or methacrylic acid monomer. The composition can additionally contain or employ other ingredients known for use in pressure sensitive adhesives including crosslinking agents, plasticizers, fillers and anti-oxidants.

The composition is prepared by mixing the drug and an essentially non-tacky polymer, namely the multi-polymer, with an elastomer, namely the rubber and a tackifying agent. The composition maintains its adhesive properties even where the drug acts as a plasticizer or solvent. The tackifying agent increases tack and adhesiveness.

Although the structure of the composition has not been analyzed, it is conceivable that the two polymers result in a heterogenous mix, the elastomer performing as an interpenetrating polymeric network in the multi-polymer.

DETAILED DESCRIPTION OF THE INVENTION

This invention is directed to multi-polymer dermal compositions suitable for transdermal drug delivery. The dermal compositions of this invention are resistant to erosion by moisture and biological fluids and yet have strong peel adhesion, shear resistance and tack qualities.

The dermal composition of this invention comprises a drug; a multi-polymer of vinyl acetate and ethylene monomers; a rubber and a tackifying agent. The multi-polymer and rubber are preferably in a ratio by weight respectively from about 1:1 to about 10:1, more desirably 1:1 to 5:1 and preferably about 3:1.

Although the multi-polymer of this invention exhibits very little peel or tack, the incorporation of relatively large amounts of the medicament or medicament in a solvent therefor, results in a strong pressure sensitive adhesive capable of effectively bonding to the skin for prolonged periods of time, even in the face of aggressive physical activity and diverse environmental conditions.

This system permits an unusually high loading of medicament into the overall pressure sensitive adhesive formulation while maintaining the desirable physical propertes. A crosslinking agent for any reactive functional groups on the polymer may optionally be used as will be apparent to one skilled in the art. Crosslinking agents for this system are those known for use in crosslinking of carboxyl groups.

The transdermal drug delivery system of this invention has a defined geometric shape, with a release liner on one side. Removal of the liner exposes the pressure sensitive adhesive that functions as the drug carrier and as the means of applyng the system to the patient. The pressure-sensitive adhesive is backed by a drug impermeable material that may be colored and labeled as appropriate. Suitable release liners and backings include those known in the art for use with pressure sensitive adhesives.

The composition of this invention possesses sufficient adhesive properties to remain in place for days with low incidence of debonding and appears, surprisingly, to increase the rate of drug delivery as compared with a marketed acrylic-based transdermal drug delivery system.

Various other types of polymers for use with nitrate vasodilators were tried without success: polyvinyl acetate copolymers other than ethylene vinyl acetate polymers, polyvinyl acetate homopolymers, acrylic-based copolymers, polyurethane and styrene-butadiene rubber. Upon addition of nitroglycerin in amounts as low as 20% by weight (dry), the resulting composition ranged in properties from a non-tacky film to a "gooey" liquid. Where a potential adhesive film did form, as with a vinyl acetate based homopolymer and with an acrylic formulation, the resulting formulation was not of adequate adhesive properties or it lacked the ability to resist moisture.

A vinyl acetate/ethylene polymer system lacking the rubber component was able to maintain structural integrity in combination with drug (or drug and a solvent therefor). When exposed to human skin it was able to resist moisture, but it did not have sufficient adhesive properties.

This invention is based on the findings that the adhesive properties of drug-containing, optionally cross-linked multi-polymers of vinyl acetate and ethylene monomers could be improved by the addition of a rubber, along with the addition of a tackifying agent, known for use in such polymers.

The dermal composition according to the present invention can be prepared, for example, by mixing the multi-polymer, drug, the rubber and tackifying agent in an appropriate liquid, preferably a polar liquid such as water, casting the mixture and removing the liquid, for example by evaporation, to form a film.

The multi-polymer of vinyl acetate and ethylene monomers can be either a copolymer or a terpolymer. Thus a copolymer of vinyl acetate and ethylene can be used. In addition, the terpolymer of an acrylic acid/vinyl acetate/ethylene can also be used. Such a terpolymer is in fact the preferred embodiment of this invention. Thus the third monomer of the terpolymer can be an acrylic acid such as acrylic acid or methacrylic acid or copolymers thereof.

Vinyl acetate/ethylene copolymers and terpolymers are well known, commercially available materials. Typically such polymers have a vinyl acetate content of about 4 percent to 80 percent by weight and an ethylene content of 15 to 90 percent of the total and a melt index of about 0.1 to 1000 grams per ten minutes. Melt index is the number of grams of polymer which can be forced through a standard cylindrical orifice under a standard pressure at a standard temperature and thus is inversely related to molecular weight. As is used in the specification, melt index is determined in accordance with the standard ASTM D 1238-65DP. Preferably the vinyl acetate/ethylene copolymer or terpolymer has a vinyl acetate content of about 4 percent to 50 percent by weight, with a melt index of about 0.5 to 250 grams per ten minutes, and a density having a range of about 0.920 to 0.980. More preferably the polymer has a vinyl acetate content of 4 percent to 40 percent by weight and a melt index of about 0.5 to 25 grams per ten minutes. The amount of the acrylic acid monomer in the carboxylated vinyl acetate/ethylene terpolymer is desirably about 0 to 5 percent.

From the foregoing it can be understood that the multi-polymer can be composed of at least about 0 to 5 percent by weight of an acrylic acid, from 15 to 90 percent by weight of ethylene monomer and from about 4 to 80 percent by weight of vinyl acetate monomer.

The vinyl acetate/ethylene multi-polymer is permeable to the drug and thus permits passage of the drug by diffusion through the polymer. Normally, the rate of passage of the drug through the polymer is dependent on the solubility of the drug therein. This means that the selection of the particular vinyl acetate/ethylene multi-polymer, along with the rubber and other agents will be dependent on the particular drug used and the form in which it is added, namely drug alone or the drug plus solvent. By varying the composition, the dosage delivery rate can be controlled as will be apparent to one skilled in the art.

In addition to varying the percentage of vinyl acetate in the multi-polymer, the properties of the polymer can be changed by varying the amount of acrylic acid The greater the amount of acrylic monomer, the greater the number of carboxyl groups and the more hydrophilic the polymer.

Selection of the particular vinyl acetate/ethylene multi-polymer is governed in large part by the drug to be incorporated in the device, as well as the desired rate of delivery of the drug. Those skilled in the art can readily determine the rate of delivery of drugs from the polymers and select suitable combinations of polymer and drug for particular applications. Various techniques can be used to determine the rate of delivery of the drug from the polymer. The rate of delivery is easily determined by measuring the rate of drug transferred from one chamber to another through cadaver skin and calculating, from the obtained data, the drug delivery or flux rate.

The term "rubber" used here means a natural or synthetic elastomeric polymer. The rubbers useful in the invention include natural latex (polyisoprene) and carboxylated styrene/butadiene polymers. Other suitable rubbers include styrene copolymers such as styrene-isoprene-styrene block copolymer, polybutylene and polyisobutylene, synthetic polyisoprene, butyl rubber and silicone rubber.

The rubber elastomers impart the properties of rubber to the composition such as extensibility and rapid recovery from modular strains. Particularly suitable elastomers include the synthetic rubbers having a molecular weight distribution approximating that of natural rubber latex or natural rubber latex itself.

The ratio by weight of multi-polymer to rubber is preferably about 1:0 to about 10:1 respectively and preferably about 1:1 to about 5:1, and more preferably 3:1, the amount of rubber used being selected to preferably achieve a tack of 200 to 800 grams per square centimeter and more preferably 300 to 500 grams per square centimeter (ASTM D 2979) and adhesion of about 1 to 3 pounds per linear inch (ASTM D 903-49).

In general, the composition should have a glass transition temperature (Tg), measured using a differential scanning calorimeter, of between about $-70°$ C. to $-0°$ C. and be a pressure senstive adhesive at room temperature.

In practicing the invention, one may use any drug capable of producing a pharmacological response, either localized or systemic in animals and plants. The active drugs that can be administered by the novel transdermal drug delivery system of this invention include, but are not limited to:

1. Cardiovascular medications, such as, nitroglycerin, isosorbide dinitrate, isosorbide mononitrates, diltiazem, nifedipine, quinidine sulfate, procainamide, clonidine, propranolol, and others;

2. Hormones, such as, androgens, estrogens, and progestational agents;

3. Anesthetics, such as, lidocaine, fentanyl, fentanyl analogues, and the like;

4. Analgesics and drugs having an action on the central nervous system, such as, salicylic acid derivatives, opiates, opioids and antagonists therefor, 5. Nutritional agents, such as, vitamins and amino acids, 6. Anti-inflammatory agents, such as, piroxicam, indomethacin, prednisilone, and steroids;

7. Antihistamines and cold-remedy entities, such as, chlorpheniramine maleate, and phenylpropanolamine;

8. Respiratory agents, such as, salbutamol and terbutaline;

9. Sedatives and hypnotics, such as chloral hydrate, benzodiazepines, and barbiturates;

10. Anti-infectives, such as, antibiotics and antivirals;

11. Dermatological agents;

12. Anti-cancer drugs;

13. Anti-diabetics, and

14. Anorectics.

Other drugs having same or different physiological activity as those cited above, may be used within the scope of this invention.

The amount of drug to be incorporated in the composition varies depending on the particular drug, the desired therapeutic effect and the time span for which the device provides therapy. For most drugs, the passage of the drugs through the skin will be the rate limiting step. Thus the amount of drug and the rate of release is typically selected so as to provide delivery characterized by a zero order time dependency for a prolonged period of time. The minimum amount of drug in the system is selected based on the rate at which the drug passes through the skin in the time span for which the device is to provide therapy. Conveniently the amount of drug in the system can vary from about 1 to about 50% by weight and preferably 2 to 40%.

The drugs in the multi-polymer, can be in different forms, depending on the form which yields the optimum release characteristics. Thus, the drugs can be in their free base or acid form, in the form of salts, esters or ethers, components of molecular complexes or pharmacologically acceptable derivatives thereof.

Tackifying agents for use in this invention are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins. Tackifying agents can be classified into those containing polar groups and those without polar groups. Tackifying agents with polar groups include natural rosin, hydrogenated rosin and derivatives thereof such as the glycerin or pentaerytritol esters. Tackifying agents without polar groups include polyterpenes and the so-called petroleum based tackifiers produced by polymerization of petroleum cracking fractions, mainly C5 to C9 cracking fractions. Tackifying agents with polar groups have an affinity for nitroglycerin and a mixture of polar and non-polar tackifying agents affects the release rate for ntroglycerin and chemically related compounds.

Useful crosslinking agents of this invention are those groups known in the art for crosslinking carboxylic acid groups including: (1) melamine formaldehyde resin, (2) urea formaldehyde resin; (3) phenolic resin, (4) glyoxal; (5) zinc oxide and magnesium oxide and (6) ammonium dichromate.

The optional inclusion of a crosslinking agent causes the formation of a three dimensional molecular lattice network, which serves to increase the structural integrity without solubilizing or otherwise interfering with the adhesve properties of the composition.

The crosslinking agent is conveniently a 85 percent triethyl melamine derivative. The optional crosslinking agent as a whole is present in the composition in an amount in the range of about 0.001 to about 2 percent by weight based on the total weight of the composition including adhesive polymer, rubber, tackifier, drug and crosslinking agent. The melamine derivative is preferably a melamine-formaldehyde polymer.

By adjusting the type and amount of polymer, rubber, drug, tackifying agent and optional crosslinking agent, it is possible to produce a composition that can be effectively utilized as a transdermal drug delivery system. The interacting effects of the drug, polymer, rubber, tackifying agent and optional crosslinking agent make it possible to improve the stability, adhesion, wear and amount of drug delivery per unit area. The desirable composition is non-irritating to the skin. Further, the composition should be sufficiently adhesive so as to firmly adhere to the skin, even when subjected to adverse conditions such as humidity, perspiration, movement, showers and/or bathing, but not so adhesive as to cause irritation to the skin or substantial discomfort to the patient when removed from the skin. Further, all components used must be compatible with the drug.

The composition can also contain agents known to accelerate the release of the drug onto the body surface or through the skin. This class of agents includes those with diverse mechanisms of action including those which have the function of improving the solubility and diffusibility of the drug within the multi-polymer and those which improve percutaneous absorption. For example, by changing the *stratum corneum's* (skin) ability to retain moisture, softening the skin, improving the skin's permeability, acting as penetration assistants or hair-follicle openers or changing the state of the skin including the boundary layer. Some of these agents have more than one mechanism of action and can, in addition, enhance the efficacy of the drug Some examples of these release enhancers are glycols such as diethylene glycol, propylene glycol or polyethylene glycol which enhance drug solubility, oils such as olive oil, squalene or lanolin which enhance drug diffusibility, urea and urea derivatives such as allantoin which affect the ability of keratin to retain moisture, polar solvents such as dimethyldecylphosphoxide, methyloctylsulfoxide, dimethyllaurylamide, dodecylpyrrolidone, isosorbitol, dimethyl-acetonide, dimethylsulfoxide, decylmethylsulfoxide and dimethylformamide which affect keratin permeability, salicylic acid which softens the keratin, amino acids which are penetration assistants, benzyl nicotinate which is a hair follicle opener, and higher molecular weight aliphatic surfactants such as lauryl sulfate salts which change the surface state of the skin and drugs administered, concomitantly which have good percutaneous absorption. Other agents include linoleic and ascorbic acids, panthenol, butylated hydroxytoluene, propyl oleate and propyl or isopropyl myristates.

As a specific example of a useful composition, the inventors have found that a carboxylated vinyl acetate ethylene copolymer with a glass transition temperature of approximately 0° C. comprising 2.5 to 3% acrylic acid, 20% vinyl acetate and 76 to 77% ethylene is particularly useful, especially in combination with natural rubber and a tackifying agent.

Some drugs, such as the vasodilator nitroglycerin, function as a plasticizer because they are soluble to a certain degree in the polymer. For drug molecules which are not readily soluble in the polymer, a cosolvent for the drug and polymer can be added. Cosolvents, such as, lecithin, retinol derivatives, tocopherol, dipropylene glycol, triacetin, propylene glycol, saturated and unsaturated fatty acids, mineral oil, alcohols, butyl benzyl pthalate, etc. are useful cosolvents in the said invention depending on the solublity of the drug chosen. The adhesive polymer/drug compositions of the invention may then be combined with the crosslinking agent.

The composition of this invention may be combined with various thickeners, fillers and other additives known for use with transdermal compositions.

The adhesive layer is backed by a material useful for preventing the escape of active ingredients from the adhesive layer; however, the backing layer should not absorb the active ingredient. This backing layer is desirably selectively permeable, for example to oxygen, with a suitable water-vapor transmission rate so that the transdermal drug delivery system will "breathe" allowing the skin to maintain a more natural state. However the backing layer may be an occlusive material, such as, metal foil (example: aluminum), polyolefin (example: polyethylene or polypropylene), polyester (example: polyethylene terephthalate), and polyamid (example: nylon, as described in U.S. Pat. No. 4,291,015, the disclosure of which is incorporated by reference).

Preferred and optimum compositions are as follows:

TABLE

| Component | PERCENT BY WEIGHT | |
|---|---|---|
| | Optimum Amount For Nitrate Vasodilator | Preferred Range |
| Carboxylated Vinyl Acetate-Ethylene Copolymer | about 30 | about 20-39 |
| Rubber | 11 | 5-20 |
| Tackifying Agent | 12 | 10-30 |
| Drug | 41 | 1-50 |
| Crosslinking Agent | less than 1 | 0-5 |
| Water | 5 | Up to 12 |
| | 100% | |

EXAMPLES

In the following examples, "Airflex" refers to a trademark of Air Products and Chemical Inc., Allentown, Pa. for a group of optionally carboxylated vinyl acetate/ethylene polymers in aqueous emulsion. "Airflex 416" is a carboxylated vinyl acetate/ethylene terpolymer and has the following properties:

| Solids | 52% min. |
|---|---|
| Viscosity (cps) | 1500-2500 |
| pH | 3.5 to 5 |
| Density | 8.8 lbs. per gal. |

The same type of polymer, "Airflex 426" has the properties:

| Viscosity (20 rpm) (cps) | 1,000-1,500 |
|---|---|
| pH | 4.5-5.0 |
| Tg (°C.) | −5 to 0 |
| Intrinsic Viscosity In Toluene | 0.3-0.4 |
| Swell Index | 17.5-22.5 |

"Airflex 400", "Airflex 405" and "Airflex 465 DEV" are trademarks of Air Products and Chemicals Inc., Allentown, Pa. for a group of vinyl acetate/ethylene copolymers supplied as aqueous emulsions. Airflex 400 has the following properties:

| Viscosity | 1900-2800 cps @ 20 rpm (77° F.) |
|---|---|
| Tg | 0° C. |
| pH | 4.0 to 5.0 |
| density | 8.9 lb per gal. |

Airflex 405 has the following properties:

| Viscosity | 300-200 cps @ 20 rpm (25° C.) |
|---|---|
| Tg | 71° C. |
| pH | 5.0 to 6.0 |
| density | 9.0 lb per gal. |

Airflex 465 DEV has the following properties:

| Viscosity | 800-1300 cps @ 20 rpm (77° F.) |
|---|---|
| Tg | −5° C. |
| pH | 4.5 to 5 |
| density | 9.0 lb per gal. |

Hartex 103 is a trademark of Firestone Synthetic Rubber and Latex Company for low-ammonia natural latex (rubber) containing 0.036% sodium dimethyldithiocarbamate and 0.036% zinc oxide as a preservative. The properties of this latex are as follows:

| Total Solids | 62.1 ± 0.3 |
|---|---|
| | 61.5 min. |
| Dry Rubber Content, % | 60.0 min. |
| TS minus DRC, % | 1.75 max. |
| Total Alkalinity, % NH on wet weight | .24 ± .02 |
| KOH Number | 0.55 ± 0.05 |
| Mechanical Stability, sec. | 1400 ± 300 |
| Volatile Fatty Acid, % | 0.05 max. |
| pH | 9.8 ± 0.20 |
| Sludge Content, % on weight | 0.03 max. |

PSA 578A is the trademark of Dow Chemical, Midland, Mich. for carboxylated styrene/butadiene containing a bactericide and a stabilizer. The formulation has a boiling point of 100° C., a vapor pressure of 17.5 millimeters of mercury at 20° C., a Tg. at −44° C. a vapor density of 0.624 at 80° F., is supplied in emulsion form with a milky white liquid appearance and has a specific gravity of 0.980–1.040.

Nitroglycerin can be supplied as glyceryltrinitrate available in an ethanol solution from Imperial Chemical Industries.

"Exxon 108A" emulsion is the trademark of Exxon Chemical Company. Baton Rouge, La. for an aliphatic petroleum resin tackifying agent having a glass transition temperature of 40° C., a ph of 7.0 and an average particle size of 0.33 microns, and an anionic particle charge.

"Exxon 109A" emulsion is the trademark of Exxon Chemical Company, Baton Rouge, La. for a mixed aromatic/aliphatic petroleum resin tackifying agent in an aqueous emulsion having a glass transition temperature (Tg) at 37° C., a pH of 7.0, with an average particle size of 0.5 microns and an anionic particle charge.

"Noven 109A" is a trademark of Noven Pharmaceuticals, Inc., Miami. Fla., for the combination of 140 parts of the anhydrous resin Exxon 109A. 70 parts toluene and 7 parts Triton X-100. Triton X-100 is a trademark of Rohm and Haas Company for the water soluble, anhydrous, nonionic surfactant octylphenoxypolyethoxyethanol with an average of 10 moles of ethylene oxide, having a viscosity of 240 cps @25° C. (Brookfield), a pour point of 7° C. or 45° F., a specific gravity of 1.065 @25° C. and a density of 8.9 lb. per gallon.

"Exxon 346" is a trademark of Exxon Chemical Company for a mixed aromatic/aliphatic petroleum resin tackifying agent having a Tg of 25° C., a pH of 7.0, an average particle size of 0.35 microns and an anionic particle charge.

"Flexbond 150" is a trademark of Air Products and Chemicals, Inc., Allentown, Pa. for a polyvinylacetate polymer which is a pressure sensitive emulsion which can function as a tackifying agent.

"Aerotex 3730" resin is a trademark of American Cyanamid, Wayne, N.Y. for a melamine formaldehyde crosslinking agent for various functional groups, including carboxyl groups having a density of 10.5 lbs. per gallon.

"Santicizer 160" is a trademark of Monsanto, St. Louis, Mo. for butyl benzyl phthalate.

All the polymeric ingredients used in the examples are supplied as aqueous emulsions wherein the percent solids are as follows:

| Ingredient | Percent Solids |
| --- | --- |
| Airflex 400 | 55% |
| Airflex 405 | 55 |
| Airflex 416 | 52 |
| Airflex 426 | 60 |
| Airflex 465 | 66 |
| Hartex 103 | 61.5 |
| PSA 578A | 49 |
| Exxon 108A | 57 |
| Exxon 109A | 57 |
| Exxon 346 | 57 |
| Noven 109A | 35 |
| Flexbond 150 | 55 |
| Aerotex 3730 | 83 |

The general method of preparation of the adhesive is per the following steps:

1. Appropriate amounts of rubber, tackifyng agent and multi-polymer at a pH of about 5 are combined, and thoroughly mixed together in a vessel;
2. The mixture of step 1 is then mixed in an appropriate amount of purified water until a homogeneous mixture of the polymer and water is obtained;
3. The homogeneous mixture is then transferred to a vessel where the drug or drug and cosolvent are to be added,
4. The drug is then added to the homogeneous mixture and agitation is carried out until the mixture and drug form a smooth, homogeneous mix;
5. The homogeneous mix containing the drug is then transferred to an adhesive mixing vessel;
6. The mix containing the drug can then be combined with a crosslinking agent and any additional optional ingredients and thoroughly agitated in order to begin the initiation of crosslinking the polymer chains;
7. The crosslinkable vinyl acetate-based adhesive containing the drug is then transferred to a coating operation;
8. The adhesive composition containing the drug is now in a form to make up the adhesive layer to be coated onto a release liner. When the adhesive composition has been coated onto the release liner, the unit is then passed into an oven in order to drive off the water and/or solvents which may have been included in the mixing procedure; and after this operation is completed and the solvents are removed, the adhesive-component layer will be joined to the backing material and the unit can be wound into rolls for storage.

The order of steps, the amount of the ingredients, pH, and the amount and time of agitation or mixing may be important to avoiding coagulation or clumping together of the components. These factors can be adjusted by those skilled in the art, while keeping in mind the object of providing a smooth, homogeneous mix. It is believed that a number of other methods, including changing some of the order of steps, can be carried out and will give desirable results. In addition to having various shapes, the dosage units produced may come in various sizes. A surface area in the range of 1 to 200 square centimeters is contemplated and the presently contemplated, preferred sizes are: 5, 10, 15, 20, 30, 40 and 60 square centimeters. The present invention allows incorporation of the amount of drug that is sufficient to deliver the required dose, no greater than the amount that would yield undesirable properties.

EXAMPLES

In the following examples, percent refers to percent by weight (dry).

EXAMPLE 1

The carboxylated vinyl acetate ethylene copolymer (Airflex 416) is adjusted to a pH of 5.0 with aqueous ammonia. This mixture is added slowly and with stirring to the rubber. Then, slowly add the tackifying agent and stir. Next the drug is added slowly and with stirring. And finally, any crosslinking agent is added and the mixture stirred. The resulting mixture is coated on to a release liner as set forth in step 8 above.

The resulting composition has the following ingredients in the indicated amounts.

| Component | PERCENT BY WEIGHT |
| --- | --- |
| Carboxylated Vinyl Acetate Ethylene Copolymer (Airflex 416) | 31.4 |
| Rubber (PSA 578A) | 8.8 |
| Tackifying Agent (Noven 109A) | 12.6 |
| Drug (nitroglycerin) | 42.2 |
| Water | 5.0 |
| | 100 |

In the following examples the method of Example 1 is used with the appropiate amounts of starting materials to yield compositions having the following ingredients.

| Component | PERCENT BY WEIGHT |
| --- | --- |
| Carboxylated Vinyl Acetate-Ethylene Copolymer (Airflex 416) | 28.3 |
| Rubber (Hartex 103) | 10.0 |
| Tackifying Agent (Exxon 346) | 18.5 |
| Drug (nitroglycerin) | 38.0 |
| Crosslinking Agent (Aerotex 3730) | 0.2 |
| Water | 5.0 |
| | 100.0 |

EXAMPLE 3

| Component | PERCENT BY WEIGHT |
| --- | --- |
| Carboxylated Vinyl Acetate- | 28.8 |

-continued

| Component | PERCENT BY WEIGHT |
|---|---|
| Ethylene Copolymer (Airflex 416) | |
| Rubber (PSA 578A) | 8.2 |
| Tackifying Agent (Exxon 346) | 19.0 |
| Drug (nitroglycerin) | 38.9 |
| Crosslinking Agent (Aerotex 3730) | 0.1 |
| Water | 5.0 |
| | 100.0 |

EXAMPLE 4

| Component | PERCENT BY WEIGHT |
|---|---|
| Carboxylated Vinyl Acetate-Ethylene Copolymer (Airflex 416) | 29.6 |
| Rubber (PSA 578A) | 8.3 |
| Tackifying Agent (Flexbond 150) | 18.7 |
| Drug (nitroglycerin) | 38.0 |
| Crosslinking Agent (Aerotex 3730) | 0.4 |
| Water | 5.0 |
| | 100.0 |

EXAMPLE 5

| Component | PERCENT BY WEIGHT |
|---|---|
| Carboxylated Vinyl Acetate-Ethylene Copolymer (Airflex 416) | 28.9 |
| Rubber (Hartex 103) | 10.2 |
| Tackifying Agent (Flexbond 150) | 18.3 |
| Drug (nitroglycerin) | 37.1 |
| Crosslinking Agent (Aerotex 3730) | 0.5 |
| Water | 5.0 |
| | 100.0 |

EXAMPLE 6

| Component | PERCENTAGE BY WEIGHT |
|---|---|
| Carboxylated Vinyl Acetate-Ethylene Copolymer (Airflex 426) | 28.3 |
| Rubber (Hartex 103) | 10.0 |
| Tackifying Agent (Exxon 109A) | 18.6 |
| Drug (Nitroglycerin) | 38.0 |
| Crosslinking Agent (Aerotex 3730) | 0.1 |
| Water | 5.0 |
| | 100.0 |

EXAMPLE 7

| Component | PERCENTAGE BY WEIGHT |
|---|---|
| Carboxylated Vinyl Acetate-Ethylene Copolymer (Airflex 416) | 28.6 |
| Rubber (Hartex 103) | 5.1 |
| Rubber (PSA 578A) | 4.0 |
| Tackifying Agent (Exxon 109A) | 18.8 |
| Drug (Nitroglycerin) | 38.4 |
| Crosslinking Agent (Aerotex 3730) | 0.1 |
| Water | 5.0 |
| | 100.0 |

EXAMPLE 8

| Component | PARTS BY WEIGHT |
|---|---|
| Carboxylated Vinyl Acetate-Ethylene Copolymer (Airflex 416) | 28.8 |
| Rubber (PSA 578A) | 8.2 |
| Tackifying Agent (Exxon 108A) | 19.0 |
| Drug (Nitroglycerin) | 38.9 |
| Crosslinking Agent (Aerotex 3730) | 0.1 |
| Water | 5.0 |
| | 100.0 |

EXAMPLE 9

| Component | PARTS BY WEIGHT |
|---|---|
| Carboxylated Vinyl Acetate-Ethylene Copolymer (Airflex 416) | 29.0 |
| Rubber (Hartex 103) | 10.3 |
| Tackifying Agent (Flexbond 150) | 18.4 |
| Drug (Nitroglycerin) | 37.3 |
| Water | 5.0 |
| | 100.0 |

EXAMPLE 10

| Component | PARTS BY WEIGHT |
|---|---|
| Vinyl Acetate-Ethylene Copolymer (Airflex 465) | 39.5 |
| Rubber (Hartex 103) | 11.0 |
| Tackifying Agent (Exxon 109A) | 20.5 |
| Drug (Nitroglycerin) | 24.0 |
| Water | 5.0 |
| | 100.0 |

EXAMPLE 11

| Component | PARTS BY WEIGHT |
|---|---|
| Vinyl Acetate Ethylene Copolymer (Airflex 400) | 53.5 |
| Rubber (PSA 578A) | 14.3 |
| Drug (Nitroglycerin) | 27.2 |
| Water | 5.0 |
| | 100.0 |

EXAMPLE 12

| Component | PARTS BY WEIGHT |
|---|---|
| Vinyl Acetate Ethylene Copolymer (Airflex 405) | 35.0 |
| Rubber (Hartex 103) | 11.7 |
| Tackifying Agent (Exxon 109A) | 21.8 |
| Drug (Nitroglycerin) | 26.5 |
| Water | 5.0 |
| | 100.0 |

EXAMPLE 13

| Component | PARTS BY WEIGHT |
|---|---|
| Carboxylated Vinyl Acetate-Ethylene Copolymer (Airflex 416) | 34.0 |
| Rubber (Hartex 103) | 12.1 |
| Tackifying Agent (Exxon 109A) | 22.4 |
| Drug (Nitroglycerin) | 26.5 |

-continued

| Component | PARTS BY WEIGHT |
|---|---|
| Water | 5.0 |
| | 100.0 |

EXAMPLE 14

The preferred embodiment for nitroglycerin is one having the optimum amounts shown in the Table set forth above just prior to the examples with the copolymer being Airflex 416, the rubber being Hartex 103, the tackifying agent being Noven 109A, and the crosslinking agent being Aerotex 3730.

EXAMPLE 15

| Component | Percent by Weight |
|---|---|
| Carboxylated Vinyl Acetate-Ethylene terpolymer (Airflex 416) | 28.2 |
| Rubber (Hartex 103) | 10.0 |
| Tackifying agent (Exxon 109A) | 18.6 |
| Plasticizer (Santicizer 160) | 36.1 |
| drug (estradiol) | 1.9 |
| crosslinking agent (Aerotex 3730) | 0.2 |
| water | 5.0 |
| | 100.0 |

EXAMPLE 16

A formulation identical to that of Example 15 is prepared except that the amount of plasticizer is reduced to 30.4% and propylene glycol is added as solvent for the estradiol in the amount of 5.7 parts.

The dosage unit of the present invention can be produced in a number of ways. It is particularly important to form the adhesive layer in a series of steps, with proper agitation and pH adjustment when necessary, so as to avoid coagulation and clumping together of any of the components. After the adhesive layer is formed, the composition making up this layer can be placed in contact with the backing layer in any manner known to those skilled in the art in order to produce the transdermal dosage system. The transdermal dosage system can be produced as follows:

Generally speaking, known methods of producing adhesive tapes can be used for the composition of this invention. These known methods including calender coating method, hot melt coating method, solution coating method, emulsion coating method and radiation cured coating method. When dealing with explosive drugs such as nitroglycerin, the solution or emulsion coating method is preferred to minimize the risk of explosion or degradation.

In the calender coating method, the multi-polymer, rubber, tackfier and other ingredients are kneaded homogeneously using open rolls, kneaders, internal mixers, etc. The materials of high viscosity have to be kneaded at elevated temperatures, usually 90° to 120° C. under high shear rate ($1 \times 10^3$ to $5 \times 10^3$ sec.$^{-1}$). In the hot melt coating method the substances with high thermal plasticity are added to the adhesives and the adhesives are coated at high velocity. In the emulsion coating method, the emulsion of the ingredients is added to the appropriate coating head and the excess solvent removed. The solution coating method is essentially the same as the emulsion coating method, except that the mixture is in solution rather than in an emulsion.

The backing member for the adhesive includes plastic films of polyethylene, vinyl acetate resins, ethylene/vinyl alcohol, ethylene/vinyl acetate copolymers, polyvinyl chloride, polyurethane, and the like, metal foils, for example aluminum foil, and the like, non-woven fabric, cloth and laminate films composed of cloth or paper and a basic film. The backing material preferably has a thickness of from 2 to 1,000 micrometers so as to have good handling properties and "feel". A total thickness of the film-like adhesive material on the backing member preferably ranges from 12 to 250 micrometers. Composite products having a total thickness less than 14 micrometers have poor handling properties.

What is claimed is:

1. An adhesive dermal composition comprising a drug, a multipolymer containing vinyl acetate and ethylene monomers, a natural or synthetic rubber, and a tackifying agent, in which the ratio by weight of the multi-polymer to rubber is about 1:1 to about 10:1.

2. The dermal composition of claim 1, in which the multi-polymer is a carboxylated vinyl acetate/ethylene terpolymer and the rubber is polyisoprene.

3. The dermal composition of claim 1 in which the drug is a solid or liquid at room temperature, is percutaneously absorbable, and is dissolved or dispersed in the composition.

4. The dermal composition of claim 3 in which the weight of the drug is about 1 to 50% by weight based on the weight of the dermal composition.

5. A dermal composition comprising a drug, a crosslinked multipolymer of carboxylated vinyl acetate/ethylene, a natural or synthetic rubber, and a tackifying agent in which the multipolymer and rubber are in a ratio, respectively, of from about 1:1 to about 10:1.

6. The dermal composition according to claim 5 in which the crosslinking agent is selected from the group of agents known for the crosslinking of free carboxyl groups of polymeric substances.

7. The dermal composition according to claim 5 in which the crosslinking agent is selected from the group consisting of melamine formaldehyde resin, urea formaldehyde resn, phenolic resins, epoxy resins, glyoxal, zinc oxide, magnesium oxide and ammonium dichromate.

8. The dermal composition according to claim 5, in which the multipolymer is a terpolymer of ethylene, vinyl acetate and acrylic acid.

9. The dermal composition according to claim 8 in which the percent by weight of ethylene, vinyl acetate and acrylic acid units in the terpolymer are, respectively, roughly 15 to 90; 4 to 80 and 0 to 5.

10. The dermal composition according to claim 8 in which the amounts of ethylene, vinyl acetate and acrylic acid are respectively roughly 77%, 20% and 3%.

11. The dermal composition according to claim 5 in which the carboxylated vinyl acetate ethylene copolymer and natural rubber are in a ratio, respectively, of about 3:1.

12. The dermal composition which comprises, as percent by weight, about 20% to about 39% carboxylated vinyl acetate ethylene copolymer about 5% to about 20% natural rubber, about 10% to about 30% of a tackifying agent, about 1% to about 50% of drug, and 0% to about 2% of a crosslinking agent.

13. The composition of claim 12 which comprises about 30% carboxylated vinyl acetate ethylene copolymer, about 11% natural rubber, about 12% tackifier and 41% drug.

14. The composition according to claim 13 in which the drug is nitroglycerin or estradiol.

* * * * *